United States Patent
Lawrynowicz et al.

(10) Patent No.: US 9,763,791 B2
(45) Date of Patent: Sep. 19, 2017

(54) FEMORAL PROSTHESIS HEAD

(71) Applicant: Howmedica Osteonics Corp., Mahwah, NJ (US)

(72) Inventors: Daniel E. Lawrynowicz, Monroe, NY (US); Haitong Zeng, Oakland, NJ (US); Zongtao Zhang, Riverdale, NJ (US); Aiguo Wang, Wayne, NJ (US); Keenan Michael Hanson, Tuxedo, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 46 days.

(21) Appl. No.: 13/760,449

(22) Filed: Feb. 6, 2013

(65) Prior Publication Data
US 2014/0222158 A1  Aug. 7, 2014

(51) Int. Cl.
*A61F 2/36* (2006.01)
*A61F 2/30* (2006.01)

(52) U.S. Cl.
CPC ........ *A61F 2/3609* (2013.01); *A61F 2/30767* (2013.01); *A61F 2002/30051* (2013.01); *A61F 2002/30107* (2013.01); *A61F 2002/30332* (2013.01); *A61F 2002/30973* (2013.01); *A61F 2002/3611* (2013.01)

(58) Field of Classification Search
CPC .. A61F 2/36; A61F 2/3609; A61F 2002/3611; A61F 2002/365
USPC .......... 623/22.42, 22.44, 23.11, 23.42, 23.43
See application file for complete search history.

(56) References Cited

U.S. PATENT DOCUMENTS

| | | | |
|---|---|---|---|
| 3,064,645 A | 11/1962 | Ficat et al. |
| 3,466,670 A | 9/1969 | Christiansen |
| 3,707,006 A | 12/1972 | Bokros et al. |
| 5,037,438 A | 8/1991 | Davidson |
| 5,037,441 A | 8/1991 | Bouvet |
| 5,735,905 A | 4/1998 | Parr |
| 6,626,948 B2 | 9/2003 | Storer et al. |
| 7,537,664 B2 | 5/2009 | O'Neill et al. |
| 7,582,117 B2 | 9/2009 | Hunter et al. |
| 8,226,728 B2 | 7/2012 | Preuss et al. |
| 8,266,810 B2 | 9/2012 | Gordon |

(Continued)

FOREIGN PATENT DOCUMENTS

| | | |
|---|---|---|
| DE | 4441033 A1 | 5/1996 |
| DE | 102004027659 Z1 | 1/2006 |

(Continued)

*Primary Examiner* — David Isabella
*Assistant Examiner* — Christine Nelson
(74) *Attorney, Agent, or Firm* — Lerner, David, Littenberg, Krumholz & Mentlik, LLP

(57) ABSTRACT

A prosthetic head for a femoral component has a metal shell with a tapered cavity. The shell has a part-spherical outer surface defining an inner portion terminating in an open end. A polymeric material completely fills the inner portion of the hollow shell extending from an inner surface of the shell to the open end. The polymeric material includes a conically tapered socket centered about the polar axis intermediate ends of the open end wherein the shell is a hollow titanium shell having an inner surface with a porous structure for receiving a portion of the polymeric material. The hollow titanium shell inner surface has at least one rib extending inwardly toward the conically tapered socket.

16 Claims, 7 Drawing Sheets

(56) References Cited

U.S. PATENT DOCUMENTS

| | | |
|---|---|---|
| 8,268,099 B2 | 9/2012 | O'Neill et al. |
| 2003/0065398 A1 | 4/2003 | Cueille et al. |
| 2007/0233266 A1* | 10/2007 | Williams et al. .......... 623/20.14 |
| 2008/0177395 A1 | 7/2008 | Stinnette |
| 2008/0288081 A1* | 11/2008 | Scrafton et al. ............ 623/20.33 |
| 2008/0319247 A1* | 12/2008 | Forbes et al. ...................... 600/9 |
| 2010/0121458 A1 | 5/2010 | Ledger et al. |
| 2011/0014081 A1 | 1/2011 | Jones et al. |
| 2011/0153025 A1* | 6/2011 | McMinn ............. A61F 2/30771 623/20.32 |
| 2013/0190889 A1* | 7/2013 | Li ............................ A61F 2/34 623/23.11 |
| 2014/0180424 A1* | 6/2014 | Dickerson et al. ........ 623/19.12 |
| 2014/0188243 A1* | 7/2014 | Zheng et al. ................ 623/23.7 |

FOREIGN PATENT DOCUMENTS

| | | |
|---|---|---|
| FR | 2800269 A1 | 5/2001 |
| GB | 719308 | 12/1954 |
| GB | 719308 A | 12/1954 |
| WO | 2004026170 A2 | 4/2004 |
| WO | 2008015286 A2 | 2/2008 |
| WO | 2012104115 | * 8/2012 |

* cited by examiner

FEMORAL PROSTHESIS HEAD

BACKGROUND OF THE INVENTION

The present invention relates to a femoral prosthesis for use in hip joint replacement procedures. More specifically the invention relates to a novel modular prosthetic head for a femoral prosthesis.

In one embodiment, the present invention includes as components a hollow ball component having a polymeric filler with a molded tapered socket for connecting the ball component to a prosthetic femoral component stem having a conically tapered trunion.

Artificial joint prostheses are widely used to restore joint mobility to patients affected by a variety of conditions, including degeneration of the joint and bone structure. Typically, the degenerated bone structure is replaced with an orthopedic implant that mimics, as closely as possible, the structure of the natural bone and performs its functions. The satisfactory performance of these implants can be affected not only by the design of the component itself, but also by the surgical positioning of the implanted component and the long-term fixation of the implant. Improper placement or positioning of the implant can adversely affect the goal of satisfactorily restoring the clinical bio-mechanics of the joint as well as impairing adequate fixation of the component when implanted.

Orthopedic implants are constructed from materials that are stable in biological environments and withstand physical stress with minimal or controlled deformation. Such materials must possess strength, resistance to corrosion, biocompatibility, and good wear properties. Also, the implants include various interacting parts, which undergo repeated long-term physical stress inside the body.

For these reasons, among others, the bone/implant interface and the connection between various parts of the implant must be durable and resistant to breakdown. This is especially important since installation of an orthopedic implant often involves an extensive medical procedure, and therefore replacement or revision of the installed implant is typically even more difficult. The requirements for the useful life of the implant continue to grow with the increase in human life expectancy and use in younger patients. As implants improve, more younger patients are considered as implant candidates. It is therefore desirable to develop implants that, while durable in their own right, minimize the difficulty of replacement or revision surgery should the implant eventually fail.

The strength and longevity of implants in large part depend on the bone/implant interface. Various methods of connection are known in the art. For example, a hip joint is a ball-in-socket joint, and includes a rounded femoral head and a cup-like socket (acetabular cup) located in the pelvis. The surfaces of the rounded femoral head and the acetabula cup continually abrade each other as a person walks. The abrasion, along with normal loading, creates stress on the hip joint and adjacent bones. If the natural femoral head or the acetabular cup is replaced with an implant, this stress must be well tolerated by the implant's bearing surfaces to prevent implant failure.

One type of hip prosthesis is a resurfacing femoral head. In this design, the natural bone neck is preserved and a hollow metal shell is implanted on the prepared head area of the femur. The inside or distal surface is covered by cancellous bone. The metal shell replaces diseased natural cartilage. Because the acetabular cartilage will wear out over time, this resurfacing is considered temporary solution and total hip replacement is eventually conducted. Hollow metal shell designs are well-known (UK 719,308, US 2010/0121458 A1). The shell is typically made of CoCr alloy. Especially, UK 719308 discloses a resurfacing prosthesis that is composed of CoCr shell filled with plastic core, where the plastic core directly contacts cancellous bone.

The total hip replacement replaces diseased cartilage with both a prosthetic femoral head and acetabular cup. One design of the femoral head is a one piece component integral with a femoral stem. In this design, the neck length is fixed, however a patient's femoral neck length may vary from person to person. Another femoral prostheses comprises a separate stem part and a head part. The neck length is easily adjusted by different offsets to fit different patient neck lengths. The modular design is easy to use, and has become popular over the past 20 years. The stem part comprises a body section for location in the intramedullary cavity of the patient's femur, and a neck section at its proximal end for carrying the modular head part. The head part comprises an outer bearing surface formed as part of a sphere, which is for articulation in a cup component implanted into the patient's acetabulum. The stem part and the head part usually are separate components. The proximal end of the neck section of the stem part comprises a conically tapered trunion and a distal side of the head part comprises a tapered bore adapted to receive the trunion. This configuration allows for the femoral stem to be more readily implanted into the femur initially, and for a particular head part to then be chosen to suit during the procedure. Multiple femoral prosthetic head parts may be provided with, for example, different offsets and diameters for mating with different diameter acetabular cups. Modular prosthetic heads are typically made of solid metal ground into a spherical shape and include a tapered socket, such as a Morse taper in a distally facing surface thereof. However, the traditional metal-on-metal taper junction may have corrosion and fretting problems, especially with a titanium stem against a CoCr head.

One solution for the taper corrosion is to change the metal head into ceramic head. Because ceramic is non-electric conducting material, there is no galvanic corrosion problem. However, ceramic heads are brittle compared to metal heads.

BRIEF SUMMARY OF THE INVENTION

One purpose of this invention is to provide a modular femoral head that engage a metal trunion on a femoral component which improves the performance and is free of corrosion. The femoral ball head has a polymeric tapered cavity and a metal or ceramic outer shell. The polymer cavity is non-electrically conductive, thus intrinsically eliminating galvanic corrosion when it mates a metallic stem taper. Also, the selected polymer is tough and wear resistant; there is no brittle fracture issue. The metal or ceramic shell provides wear resistance when it articulates against the acetabulum such as against natural cartilage or a prosthetic bearing made of UHMWPE or ceramic. Therefore, the present invention has the overall advantage over the current metal-on-metal and ceramic-on-metal modular design.

Use of a polymer such as Polyetherether ketone (PEEK) produced a low corrosion current of a PEEK-on-metal taper trunion and reduced crevice corrosion in certain conditions. In an alternate embodiment a PEEK sleeve was placed on a Ti6Al4V stem taper. The PEEK sleeve mated with a CoCr female trunion. In another embodiment a PEEK coated Ti6Al4V stem taper was a mirror polished PEEK surface. In another embodiment PEEK was machined into a sleeve and polished.

The above aspects of the invention are provided by a prosthetic head for a femoral component having a hollow, preferably titanium, shell having a thickness between 0.2 and 3.0 mm. The shell has a part-spherical outer surface defining an inner portion terminating in a flange extending inwardly towards a polar axis of the hollow shell. A polymeric material, such as PEEK, fills the inner portion of the hollow titanium shell extending from an inner surface of the shell to an inwardly facing surface of the flange or open end. The polymeric material includes a conically tapered socket formed therein centered about the polar axis intermediate radially spaced ends of the flange on the hollow titanium shell. The hollow shell may have an inner surface with a porous structure for lockingly receiving a portion of the polymeric material. The hollow shell inner surface may have at least one rib extending from an inner surface inwardly toward the conically tapered socket for lockingly receiving the polymer. The outer surface of the hollow titanium shell may be polished or coated with a ceramic. The polymeric material may be polyetheretherketone or polyetherketoneketone or other suitable polymers. The polymeric material may be glass or carbon fiber reinforced such as with chopped fibers. The conically tapered socket may have a polished inner surface or may be molded. The at least one rib on the inner spherical surface of the head may be generally perpendicular to the inner surface of the hollow titanium shell. The ribs may extend in the longitudinal or latitude direction and are spaced at predetermined intervals. The rib may include an inner flange extending perpendicular to the rib, these being "T" shaped.

The above designs can be more expressed in the following table as combination of the options.

| Example | Shell material | Interlock structure | Core material | Bearing surface |
| --- | --- | --- | --- | --- |
| 1 | Ti6Al4V | 3D foam by additive manufacturing | PEEK | TiO2* |
| 2 | Ti6Al4V | 2D foam by PVD CoCr | PEEK | CoCr |
| 3 | CoCr | 3D by E-beam | PEK | CoCr |
| 4 | 316 L | 3D by E-beam | PEEK | 316L |
| 5 | Zr alloy | 3D foam by additive manufacturing | PPS | ZrO2 |
| 6 | Ti6Al4V | 2D surface by CVD | PEEK | Al2O3 |
| 7 | Ti6Al4V | 2D surface by PVD CrN | PEI | CrN |
| 8 | Al2O3 | 2D surface by PVD CrN | PEKK | Al2O3 |
| 9 | ZrO2 | 2D surface by PVD CoCr | PEK | Zr2O3 |

*This can be done by the process of U.S. Pat. Nos. 8,268,099 and 8,266,810

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The invention will be described in more detail below with reference to the embodiments shown in the drawings wherein.

DETAILED DESCRIPTION

In describing the preferred embodiments of the subject matter illustrated and to be described with respect to the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1:
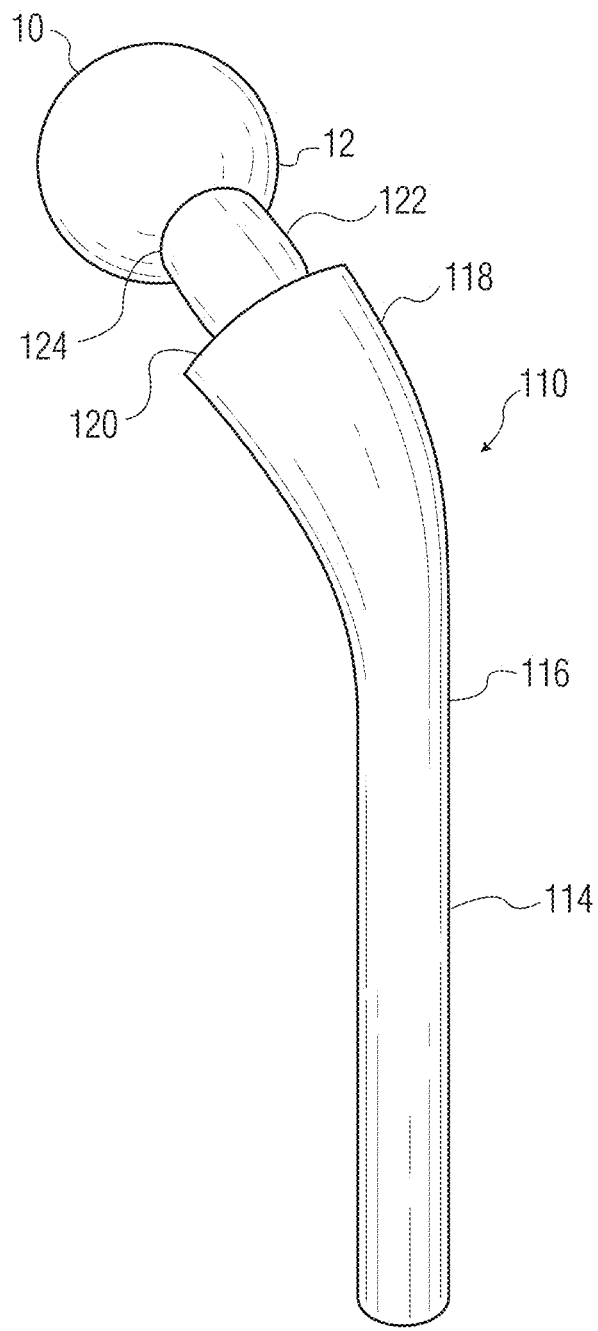
FIG. 1 shows an isometric view of a typical modular prosthetic hip implant including a femoral component having a stem, a neck and a hollow spherical prosthetic femoral head.
Figure 2:
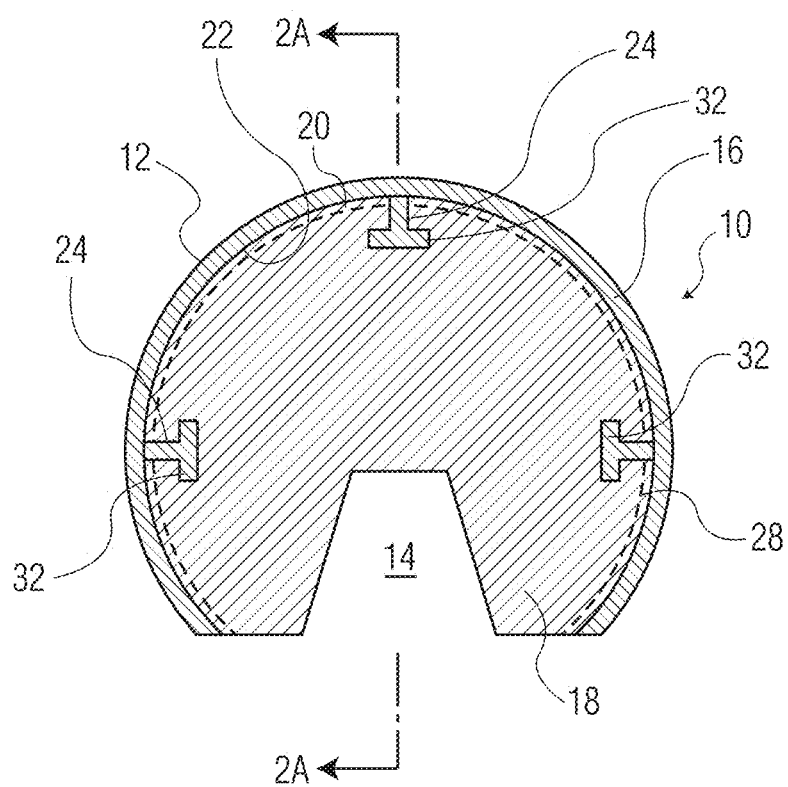
FIG. 2 shows a cross-sectional view of a spherical head of FIG. 1 including an outer shell and an inner polymer filled part spherical cavity including a conically tapered recess and a rib structure.
Figure 3:
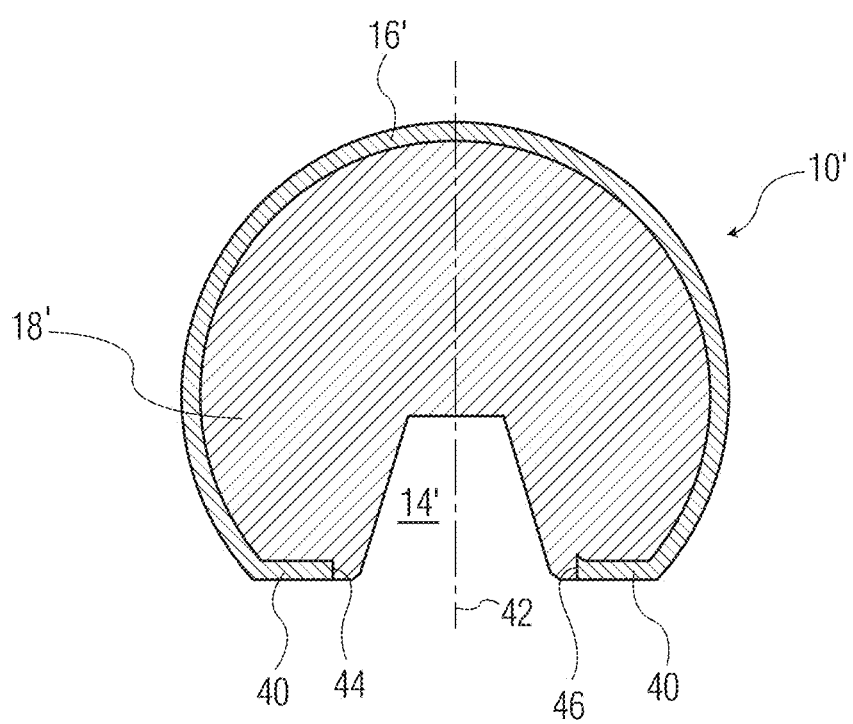
FIG. 3 shows a cross-sectional of an alternate embodiment of a part spherical head including an outer metal shell filled with a polymeric material including a trunion formed therein with a retaining flange extending from a distal end of the prosthetic femoral head.

Referring to the drawings, wherein like reference numerals represent like elements, there is shown in FIGS. 1-3, in accordance with various embodiments of the present invention, more particularly in FIG. 1, a femoral implant generally denoted as 110 used during a total hip replacement. Implant 110 includes a modular femoral head 10 having an outer surface 12 which is part-spherical in shape and adapted to engage a part-spherical cavity in a prosthetic acetabular implant. As is typical in modular implants 110, the femoral component includes a distal stem portion 114, a mid-stem portion 116 and a proximal stem portion 118. A neck 122 extends proximally from upper surface 120 of proximal stem portion 118 and has a conically tapered trunion or spigot 124 adapted to form a taper lock within a conically tapered cavity within ball or head 10. The conically tapered cavity is shown in FIGS. 2 and 3 and denoted as 14, 14' respectively.

As best shown in FIG. 2, femoral head 10 is preferably formed from two separate parts a metal or ceramic shell 16 and a polymeric support 18. Support 18 is interposed within shell 16 and forms a tapered trunion engaging cavity or socket 14. The outside surface 20 of polymeric support 18 is designed to substantially mate with inside surface 22 of shell 16. Shell 16 forms articulating surface 12, and preferably has a thin, substantially uniform thickness such that the shape of inside surface 22 substantially matches that of articulating surface 12. Accordingly, polymeric support 18 provides a majority of the appropriate spacing between articulating surface 12 and trunion engaging surface 14.

Various materials can be used in formation of part-spherical shell 16 and inner support 18. Acceptable materials for shell 16 include various metals, such as titanium, CoCr, stainless steel (SS) and titanium alloys, or a ceramic material, such as alumina. Also a metal shell can be coated with ceramic such as alumina. If a polymeric material is used to form support 18, the polymer may be reinforced with carbon or glass fiber, including long, short or micro fibers, as they are known in the art. Preferably, shell 16 is formed from a metal, such as titanium or titanium alloy, CoCr or SS having a thickness between about 0.2 mm and about 3.0 mm. In a preferred embodiment, shell 16 is formed from titanium and has a thickness of about 2 to 3 mm.

Various materials may also be used in the formation of polymeric support 18. Acceptable materials for support 18, include polymeric materials including ULTEX®, PEEK, polycarbonate, polysulphone, XYLAR®, LEXAN® and PEKK. In one embodiment of the present invention, support 18 can be made from a fiber-reinforced polymeric material. Such materials may include PEEK reinforced with carbon fibers, which may comprise long, short or micro fibers. Further, shell 16 is preferably formed with a series of inwardly extending ribs 24 therein. Ribs 24 may increase the overall strength of shell 16 and, thus, of femoral head implant 10, allowing for less-rigid and, possibly, less expensive materials to be used for support 18. Still further, the inclusion of ribs 24 allows the material from which support 18 is formed to have a more uniform thickness. This is advantageous when forming support 18 using an injection molding process because uniform material thickness allows the material throughout the entire part to cool (and thus, shrink) uniformly. This helps prevent the part from warping during cooling.

In a preferred embodiment of implant 10, shell 16 is formed from a metal, preferably titanium or titanium alloy and support 18 is formed from a polymeric material, preferably PEEK. In such an arrangement, shell 16 is more preferably formed using a hydroform process. Hydroforming is a process that is generally known in the art and is useful for imparting complex, three-dimensional ("3D") shapes into metal. Preferably, shell is formed using a vertical hydraulic hydroforming press. Such a process can be carried out by Aero Trades Manufacturing, located at 65 Jericho Turnpike, Mineola, N.Y. It is preferred that a metal subjected to a hydroform process is thin enough to be accurately formed by the process. It is also preferred that the material be thick enough to retain the shape imparted therein. The ideal thickness for shell in this embodiment will vary by the material and specific geometry used and will be known by those having reasonable skill in the art as indicated above 0.2 to 3 mm is acceptable. The use of a hydroform process to form shell 16 reduces the need for the additional process steps of CNC grinding or polishing, as are needed with a casting process.

Generally, the combination of a shell 16 made from hydroformed metal and a support 18 made from a polymeric material allows for an implant 10 which is appropriately shaped and sufficiently rigid to provide an acceptable femoral component head, while being lightweight and cost-effective from a manufacturing standpoint. Further, the cost-effective manufacture of such implants makes it reasonable to use each of such implants in only one surgical procedure or, alternately, as a trial femoral head. The provision of such disposable trial implants eliminates the need to design such an implant to withstand multiple autoclave cycles, and to withstand multiple trial reductions, further lowering the manufacturing cost thereof.

Shell 16 may be affixed to support 18 by a variety of methods, including using adhesives. Additionally, fixation may be done by providing inner surface of shell 16 with a porous metal coating 28 such as described in U.S. Pat. No. 7,537,664 or U.S. Publication No. 2011/0014081, the disclosures of which are incorporated herein by reference, to secure shell 16 to support 18. Further, in addition to ribs 24, corresponding tabs may be formed in appropriate portions of shell 16 and support 18 to achieve fixation therebetween.

An integral formation of rib or ribs 24 on the inner surface 22 of shell 16 increases the rigidity of shell 16, and accordingly of implant 10 overall. Rib 24 may be formed in a metal shell 16 by hydroforming.

As shown in FIG. 2, shell 16 further includes a flange portion 32 extending perpendicularly from the end surface of rib 24. Portion 32 further increases the rigidity of shell 16 and implant 10. Additionally, flange portion 32 provides for an additional means of affixation between support 18 and shell 16. In particular, in a preferred embodiment of the present invention, shell 16 is formed from hydroformed metal, preferably and support 18 is formed from PEEK. In this embodiment of FIGS. 2 and 3, support 18 is formed by molding the polymeric material onto the inner surface of shell 16. In such a process, support 18 may be formed by injection-molding of a polymeric material into an appropriately shaped mold into which a pre-formed shell 16 has been inserted. Because the molten polymeric material can easily flow into and around any geometry formed in the shell, including ribs 24 or porous portion 28 and flange portion 32, direct contact between the polymeric support 18 and the shell 16 may be the primary method of attachment therebetween. Incorporation of rib 24 and flange portion 32 furthers this attachment because the polymer flows into the shell, fully encasing the flange portion 32. This direct contact between the two materials along the periphery of the shell provides sufficient purchase to fully affix the support 18 to shell 16. The cavity is then machined into the head.

Referring to FIG. 3, an alternative embodiment of the present invention is shown as an implant 10' generally similar in structure to those discussed with respect to FIG. 2. Head 10' a thin metal shell 16' similar to that described above with regard to FIG. 2 with the exception that the distal portion of the shell includes an annular flange 40 extending radially inwardly towards a polar axis 42 of head 10'. Ends 44 and 46 of flange 40 are spaced sufficiently to allow for the formation of a conically tapered socket 14'. Again a polymeric support 18' is utilized to make shell 16' rigid and allow for the formation of socket 14'. As discussed above, although not shown in FIG. 3, head 10' can include ribs 24 with or without end section 32 extending perpendicular to the longitudinal extent of ribs 24.

As stated above, the inner surface of the socket 14, 14' may be polished to allow the formation of a locking taper with the conically tapered trunion of the femoral component. The locking tapers may be a Morse taper junction within the contacting smooth tapered surfaces providing a sufficient locking force to couple the head to the femoral component trunion. Support 18 is made from polymeric reinforced carbon fiber. Carbon fiber is a reinforcing fiber known for its lightweight, high strength and high stiffness. Carbon fiber is produced by a high-temperature stretching process of an organic precursor fiber based on polyacrylonitrile ("PAN"), rayon, or pitch in an inert atmosphere at temperatures above 1,800 degrees, Fahrenheit. Fibers can be transformed by removing more non-carbon atoms via heat treating above 3,000 degrees Fahrenheit. After these fibers are produced, they can be utilized in many different forms. They can be woven into long, dry fabric, pre-impregnated with PEEK resin, wound onto spools for use in filament winding, or braided and chopped into small fibers. There are several ways in which to produce components using carbon fiber; however, all of such processes require the use of a mold to impart the necessary geometry into the carbon fiber. The mold used in such a process defines the shape of the component. Accordingly, any component that can be molded can be formed from carbon fiber reinforced PEEK.

Molding processes used to form support 18 from carbon fiber include injection molding, autoclave molding, compression molding, bladder molding or resin transfer molding ("RTM"). Any of these methods can be used to produce knee femoral trials for total hip replacement (THR) and hip stem trials for THR. All of these types of molding processes force the carbon and resin to conform to the desired shape using heat and/or pressure. Once the part has cured, it maintains its shape permanently and the composite construction provides sufficient rigidity to allow the implant 10 to perform equivalently to a solid metal prosthetic femoral head having a metal conically tapered bore for receiving a conically tapered trunion on a femoral component neck/stem.

The socket 14, 14' can be made during the molding operation by placing a conically tapered metal thimble in the mold. The thimble may have a machined surface of may have a polished tapered outer surface. The thimble tapered outer surface which, after injection molding the head/shell with PEEK, forms a socket with a similar surface finish. Alternately, the tapered socket can be machined and optimally polished.

A white light microscopy was used to measure surface roughness profile (FIG. 4) of the socket. The as-machined PEEK surface profile was peak height 9.4 µm, valley −9.6 µm, average surface roughness (Ra) 1.3 µm, and the sum of peak and valley (PV) 19.0 µm. The polished PEEK surface profile was peak height 0.4 µm, valley −0.3 µm, average surface roughness (Ra) 0.04 µm, and the sum of peak and valley (PV) 0.7 µm. A fatigue galvanic corrosion experiment was conducted in simulated body fluid at room temperature under normal body walking load profile in MTS machine. After a 5 million cycle test, the electropolarization of corrosion current was recorded and the components were visually inspected. It was shown that (1) as-machined PEEK sleeve significantly decreased corrosion current as compared to a no sleeve situation; (2) the titanium alloy stem taper had crevice corrosion when using a PEEK sleeve made by direct coating and the PEEK with a polished surface, had black colored areas in the taper area. However, the as-machined PEEK sleeve did not show any black color areas, i.e., no crevice corrosion occurred. These results indicated the as-machined PEEK surface is better than the polished surface. Intimate contact between PEEK and titanium is not good in the taper/trunion area. This may be attributed to the as-machined surface has high (at least 5 µm) peaks and low (at least 5 µm) valleys when compared to a polished surface, which provide a channel allowing body fluid to enter and leave the trunion/taper area. Thus crevice corrosion was prevented.

Figure 5:
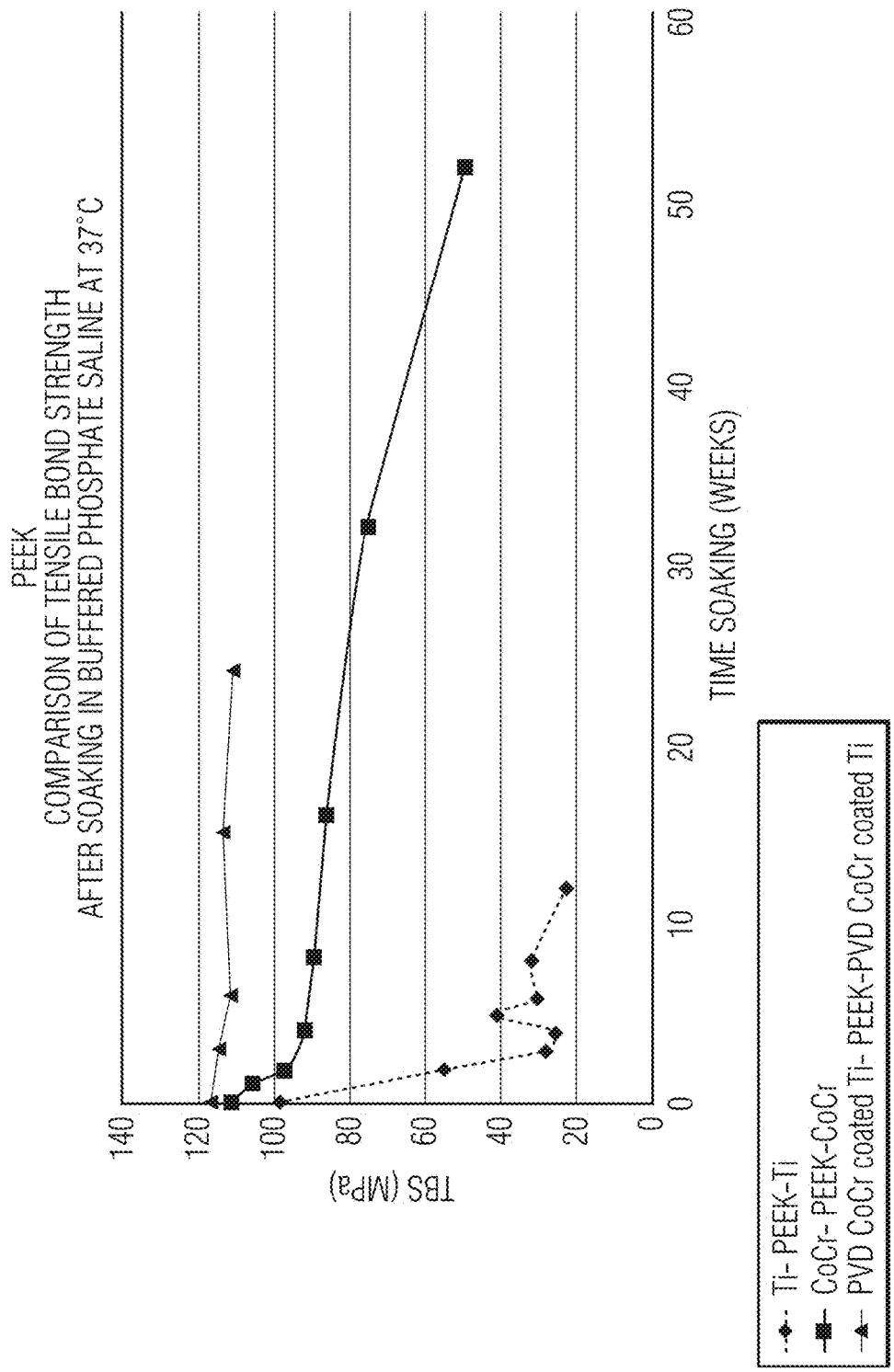
FIG. 5 shows the tensile bond strength of a PEEK bonding titanium results soaked in simulated body fluid at 37° C.
Figure 6:
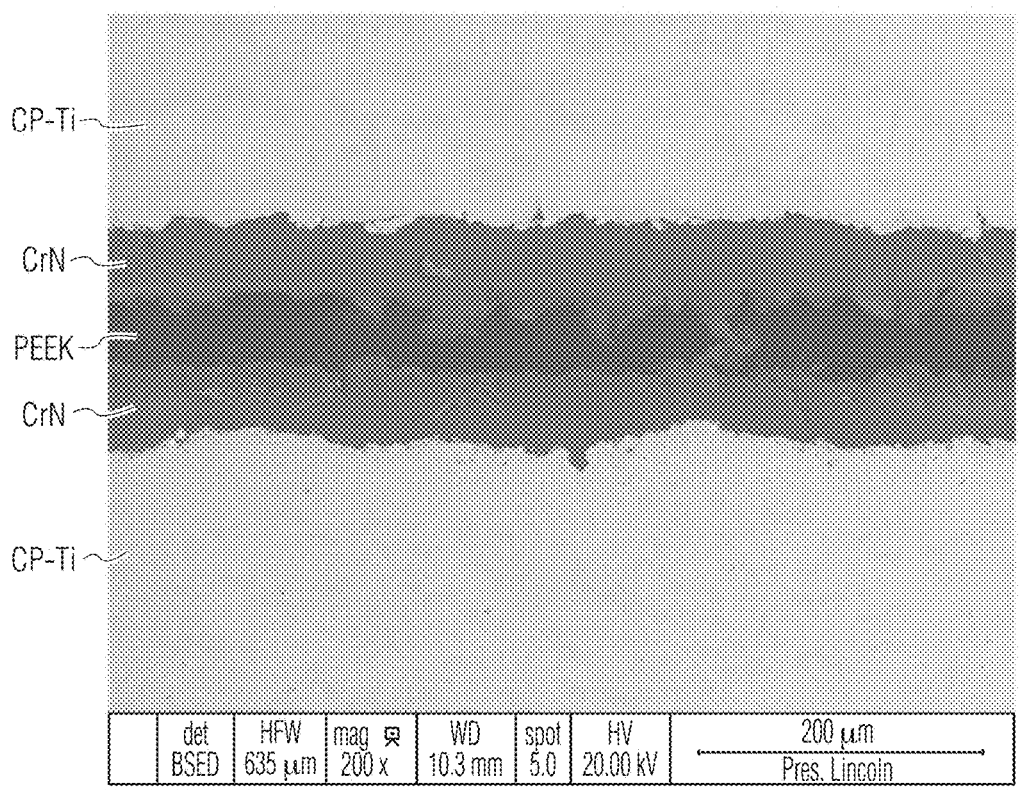
FIG. 6 shows the mechanical locking provided by PVD CrN coating for PEEK bonding to chemically pure titanium (CP-Ti).

The second finding related to interface hydrolysis. Two metal plugs were bonded with PEEK by melting PEEK film at about 385° C. in between the two metal plug in an Ar atmosphere. After cooling to room temperature, the bonded plugs were soaked in simulated body fluid (Phosphate Buffered Saline) at 37° C. The results are summarized in FIG. 5. It was found that the bonding strength was as high as 110 MPa before soaking. After soaking however, the bonding strength dropped quickly over soaking time. For Example, for alumina grit blasted Ti6Al4V plugs, bond strength decreased to 20 MPa at 4 weeks soaking. The grit blasted CoCr decreased the bond strength to about 60 MPa at 52 weeks soaking. PEEK bonding to sintered and polished alumina (>99% purity, >98% density) was also tested. Bonding strength dropped to about zero MPa after soaking in Phosphate buffered saline at 37° C. about 3 weeks (not shown in FIG. 5.) It was unexpectedly found that using a physical vapor deposition (PVD) CoCr or Chromium Nitride (CrN) coating on grit blasted titanium plugs, that the tensile bonding strength did not drop at all at 25 weeks soaking. Each data point in FIG. 5 is an average of at least two test results. FIG. 6 shows a SEM picture of PVD CrN coating on chemically pure titanium with PEEK bonding Note that the PVD CoCr has average surface roughness about 5 micrometer.

Based on the above, a femoral head was designed that has two unique features, a PEEK trunion with as-machined surface roughness and a metal or ceramic shell with mechanical locking feature in the inner surface. The as-machined trunion surface prevents crevice corrosion of the titanium metal stem taper, while the shell inner mechanical locking feature will overcome the hydrolysis issue.

In one embodiment of the invention a shell is made first and then PEEK is molded into the interior space of the shell. The shell may be made of a metal or sintered ceramic with a thickness of 0.2 to 3.0 mm. The metal shell may be made by forging, laser or E-beam additive manufacturing or by Metal Injection Molding (MIM) or hydroforming or any other relatively inexpensive process. The ceramic shell may be made by slip casting, injection molding, and cold isostatic pressing followed by normal sintering or a hot isostatic press sintering process. The outer head surface is ground/machined then polished. The metal surface may be a neat metal alloy that has good biocompatability, good wear resistance, and corrosion resistance, such as CoCr and special stainless steel. If the metal shell does not have good wear resistance such as Titanium alloy and zirconium alloy, the metal shell should be coated with a wear resistant coating. The wear resistant coating may be selected from a ceramic or metal. The ceramic coating may be alumina, zirconia, titanium oxide, chromium oxide, silicon nitride, titanium nitride, chromium nitride, diamond-like coating (DLC), diamond, titanium carbide, zirconium carbide, chromium carbide, etc. The metal coating may be CoCr, stainless steel, chromium. In addition to coating, the outer surface of the metal shell can be transformed to create a ceramic coating with a surface treatment (Sonova LLC, Long Island City, N.Y.)) or transformed with an additional ceramic sprayed or PVD coated with nano-ceramic. A process disclosed in U.S. Pat. No. 5,037,438 or U.S. Pat. No. 7,582,117 may also be used.

The metal or ceramic shell should have a mechanical locking feature. The locking feature should have an average surface roughness of at least 5.0 micrometer, which is the current grit-blasted metal surface roughness. The method to achieve the mechanical locking feature may be selected from selective laser or e-beam additive manufacture process, which can generate a three-dimensional (3D) interlock structure. The 3D structure has interconnected pores that allowed polymer to be molded into it, thus form strong mechanical locking. Another method is physical vapor deposition (PVD). A CoCr, Mo, Ta, Cr, W, Pt, Au, Ag coating can be coated by a PVD method to create two dimensional (2D) surface roughness which has some undercuts to form mechanical interlocks. Grit blasting does not produce undercuts only increased surface area. 2D surface has porosity on its surface only, while the surface pores hold polymer well to form strong mechanical lock. The inner surface may have some anti-rotation fins or ribs around the inside as well. This mechanical locking feature has been disclosed in US 2007/0233266. A 3D porous structure, 2D porous layer, and ribs can provide enough mechanical bonding strength to polymer and overcome hydrolysis issue.

The interlocking feature may vary according to the prosthesis size, shell thickness, and trunion diameter and depth. The 3D porous structure may have interconnected porosity 30-80%, preferably 40-70% and more preferred 50-65%. The 2D locking feature may have a surface roughness minimum of 5 micrometer, preferred more than 10 microns. More preferred more than 20 micrometer. The rib structure can be designed to different patterns. The preferred pattern has T-shape thus that can hold polymer from shrinking back after molding.

No matter what kind of locking feature or design details, the shell-core structure should not have any gap between polymer and shell after manufacturing. It is desirable that the tensile bonding strength between the shell and polymer should more than 35 MPa after soaking in body fluid for life time.

The polymer may be injection molded to form the interior volume and taper junction and the inside of the shell can be textured by grit blasting or left smooth. Advantages are low cost of manufacturing (avoid grinding taper geometry). The polymer taper bore eliminates fretting corrosion concerns at the junction with the trunion on the neck. Light weight saves on shipping and packaging. Burst (fracture) concerns for head are eliminated and fewer metal ions are produced during use. Such a polymer may be selected from polyaryletherketone (PAEK, including PEEK, PEKK, PEK, PEKKEKK), polyphenylene sulfide (PPS), polyacetal (POM), polyamideimide (PAI), liquid crystalline polymers (LCP), polyaryether (PAE), polyarylsulfone (PAS), polyether sulfone, polyetherimide. Of all these polymers, PAEK is the preferred polymer because its semicrystalline nature, POM, and PPS, whose hardness and fracture toughness can be adjusted by controlling crystallinity. The more preferred PAEK polymer is PEEK, which can be sterilized by current popular methods such as gamma ray, X-ray, e-beam, ETO, and autoclave. The desired PAEK polymer will have molecular weight (Mw) more than 80,000 g/mol, more preferred Mw more than 100,000 g/mol, the most preferred Mw more than 110,000 g/mol. The higher the molecular weight, the higher the polymer toughness. Because the polymer socket mates with metal taper, a micromotion and wear may occur at taper junction, high toughness of the polymer is required, which guarantees no catastrophic fracture which can occur with a bulk ceramic head. If the molecular weight is lower than 80,000 g/mol, the polymer will be brittle and is not preferred application for the taper trunion, whose behavior is more similar to ceramic.

For semi-crystalline polymers, the toughness can be as high as metal, or as low as ceramic. The key controlling factor is crystallinity. For a head application, the preferred crystallinity is lower than 50%. The corresponding polymers are LTI 1, LT2, and LT3 (Invibo Ltd, UK) or equivalent PAEK. More preferred crystallinity is lower than 40%, such as LT1 and LT 2 PEEK or equivalent PAEK. The most preferred polymer is less than 31%, which is corresponding to LT1 PEEK or equivalent PAEK.

Because the polymer is used against a metal tapered trunion, a neat polymer is preferred, i.e., not carbon fiber or glass fiber, or Barium sulfate reinforced polymer, especially not reinforced PAEK. The reason is that the reinforcement acts as a third body wear surface, which speeds up the damage to the metal taper in wet and warm corrosive body fluid.

As discussed above, in order to eliminate crevice corrosion, the mold used for injection molding PAEK should have non-polished surface. As-machined mold surface is preferred. This rough mold surface will result in a rough PEEK surface. When mating with a metallic stem taper, the body fluid and oxygen can enter and leave the taper junction freely.

Another embodiment of the invention is to make plastic (PEEK) core first, then applying a metal or ceramic shell second. In this embodiment, the inner shell mechanical locking feature and plastic trunion surface roughness may keep the same of the first embodiment, just manufacturing order was reversed.

Although the various embodiments of the present invention have been discussed as they apply either to the human knee and hip joints, one having reasonable skill in the art upon reading this disclosure would understand that the present invention can be used to form other joints of human or animal bodies. Such joints may include the elbow, wrist, shoulder, etc.

Figure 2A:
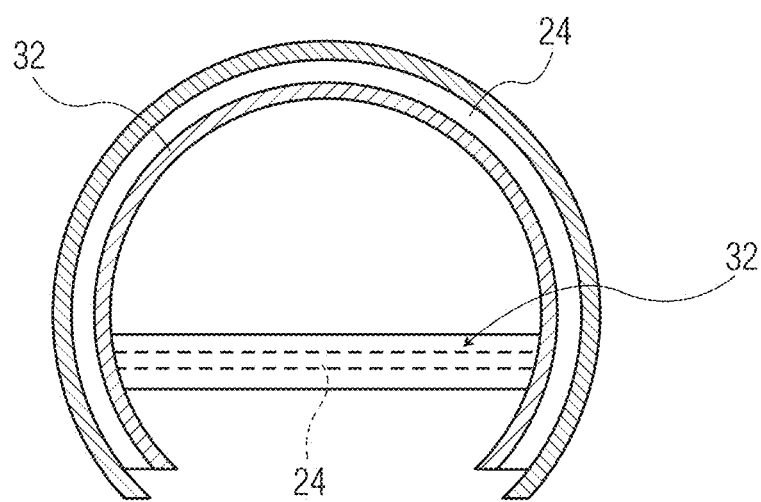
FIG. 2A is a cross-sectional view of FIG. 2 along lines 2A-2A.
Figure 4:
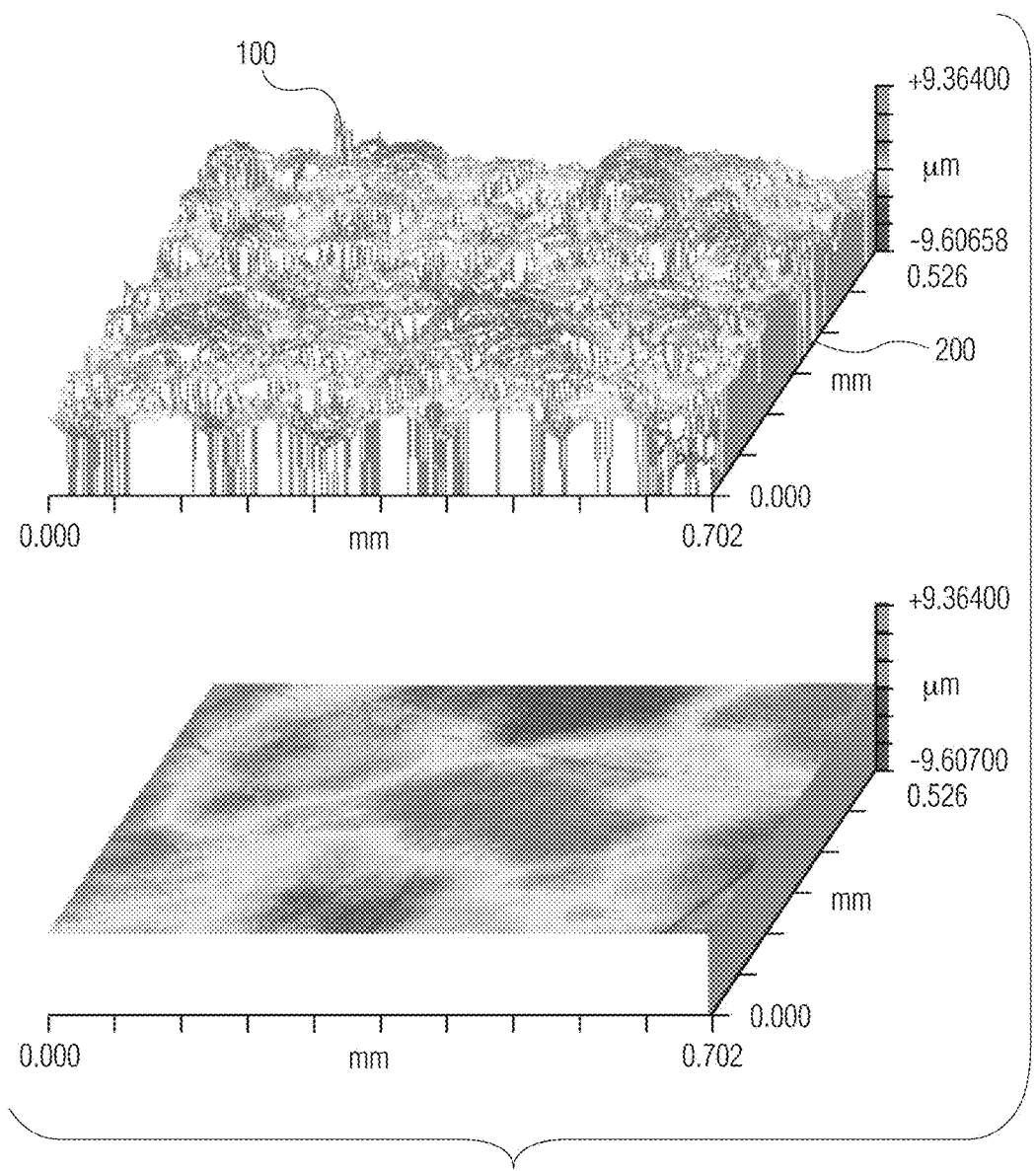
FIG. 4 shows a comparison of surface roughness profile (a) as-machined PEEK sleeve surface (top picture) and (b) shows a polished PEEK sleeve surface (bottom picture)

As seen in FIG. 4 (upper figure), the conically tapered socket has a machined inner surface comprising multiple fluid-flow channels which are formed by peaks 100 and valleys 200 greater than 5 μm in height and depth and, as shown in FIG. 4, are 9.4 μm in height and −9.6 μm in depth. The ribs 32 extend around a circumference of the inner surface of the shell as shown in FIG. 2A. When the mechanical locking structure is a roughened inner surface with an average surface roughness of 5 micrometers the surface roughness produces a bond strength above 35 MPa.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic head for a titanium femoral component comprising:
   a metal or ceramic shell with a cavity, the shell having a part-spherical outer surface centered around a polar axis, the cavity defining an inner hollow portion terminating in an open end, the polar axis extending through the open end, the polar axis perpendicular to an equator of the part-spherical shell outer surface; and
   a polymeric material filling the inner hollow portion of the shell extending from an inner surface of the shell to the open end, the polymeric material including a conically tapered recess centered about the polar axis and with a wider portion open to the open end of the shell, and the conically tapered recess having an inner conically tapered surface with an average surface roughness (Ra) of 1.3 μm.

2. The prosthesis head as set forth in claim 1 wherein the inner surface of the shell has a mechanical locking structure for receiving a portion of the polymeric material.

3. The prosthetic head as set forth in claim 2 wherein the mechanical locking structure on the shell inner surface has at least one rib extending inwardly toward the conically tapered socket.

4. The prosthetic head as set forth in claim 3 wherein the hollow shell is made of titanium and the at least one rib is generally perpendicular to the inner surface of the hollow titanium shell.

5. The prosthetic head as set forth in claim 4 wherein the at least one rib includes an inner flange extending perpendicular to the rib.

6. The prosthetic head as set forth in claim 4 wherein the at least one rib extends around the inner surface of the shell in a longitudinal or latitudinal direction with respect to the polar axis.

7. The prosthetic head as set forth in claim 2 wherein the mechanical locking structure is a roughened inner surface with an average surface roughness of more than five (5) micrometers.

8. The prosthetic head as set forth in claim 7 wherein the surface roughness produces a bond strength above 35 MPa.

9. The prosthetic head as set forth in claim 1 wherein the outer surface of the hollow shell is titanium alloy with a wear resistant ceramic or metal coating.

10. The prosthetic head as set forth in claim 1 wherein the polymeric material is selected from PEEK, PEKK, PEK, PEKKEKK, polyphenylene sulfide (PPS), polyacetal (POM), polyamideimide (PAI), liquid crystalline polymers (LCP), polyaryether (PAE), polyarylsulfone (PAS), polyether sulfone, polyetherimide.

11. The prosthetic head as set forth in claim 10 wherein the polymeric material is polyaryletherketone with crystallinity less than 40%.

12. The prosthetic head as set forth in claim 10 wherein the polymeric material is polyarylether ketone having average number molecular weight (Mw) more than 80,000 g/mol.

13. The prosthetic head as set forth in claim 1 wherein the conically tapered recess inner conically tapered surface is a machined surface comprising peaks and valleys.

14. The prosthetic head of claim 13 wherein the pathways are formed by peaks and valleys greater than 5 μm in height and 5 μm depth.

15. The prosthetic head as set forth in claim 14 wherein the peaks and valleys are 9.4 μm in height and 9.6 μm depth respectively.

16. A prosthetic head for a titanium femoral component comprising:
  a hollow titanium shell with a cavity, the shell having a part-spherical outer surface defining an inner hollow portion terminating in an open end;
  a polymeric material filling the inner hollow portion of the shell extending from an inner surface of the shell to the open end, the polymeric material including a conically tapered recess centered about the polar axis intermediate ends of the open end, the wider portion of the recess open to the open end of the shell;
  wherein the conically tapered recess having an inner conically tapered surface with an average surface roughness (Ra) of 1.3 μm;
  wherein the shell inner surface has at least one rib extending generally perpendicular to the inner surface of the hollow titanium shell;
  wherein the at least one rib includes an inner flange extending perpendicular to the rib; and
  wherein the at least one rib extends around the inner surface of the shell in a longitudinal or latitudinal direction.

* * * * *